United States Patent [19]

Kaplan et al.

[11] Patent Number: 5,352,608
[45] Date of Patent: Oct. 4, 1994

[54] BIOREDUCTION OF METAL OXIDES AND OXYANIONS BY PHOTOSYNTHETIC BACTERIA

[75] Inventors: Samuel Kaplan, Kingwood; Mark D. Moore, Houston, both of Tex.

[73] Assignee: The Board of Regents, The University of Texas, Austin, Tex.

[21] Appl. No.: 820,116

[22] Filed: Jan. 13, 1992

[51] Int. Cl.⁵ .................. B09B 3/00; C12S 13/00; C01B 19/02; C22B 5/00
[52] U.S. Cl. .................. 435/262; 435/262.5; 423/510; 75/392
[58] Field of Search .............. 435/262.5, 821, 262, 435/170; 423/510, DIG. 17; 75/392

[56] References Cited

U.S. PATENT DOCUMENTS 4,910,010 3/1990 Khalafalla ............... 435/262

OTHER PUBLICATIONS

Doran, J. W., "Microorganisms and the Biological Cycling of Selenium," *Adv. Microbiol. Ecol.,* 6:1–32, 1982.
Donohue, Timothy J., and Kaplan, Samuel, "Genetic Techniques in *Rhodospirillaceae,* "*Methods Enzymol.,* 204:459–485, 1991.
Gerhardt, Matthew B. et al., "Removal of Selenium Using A Novel Algal-Bacterial Process," *Res. J. Water Pollut. Control Fed.,* 63:799–805, 1991.
Long, Robert H. B. et al., "Selenium Immobilization in a Pond Sediment at Kesterson Reservoir," *J. Environ. Qual.,* 19:302–311, 1990.
Maiers, D. T. et al., "Selenate Reduction by Bacteria from a Selenium-Rich Environment," *Appl. Environ. Microbiol.,* 54:2591–293, 1988.
Moore, Mark D., and Kaplan, Samuel, "Identification of Intrinsic High-Level Resistance to Rare-Earth Oxides and Oxyanions in Members of the Class *Proteobacteria:* Characterization of Tellurite, Selenite, Rhodium Sesquioxide Reduction in *Rhodobacter sphaeroides,*" *J. Bacteriol.,* 174(5):1505–1514, 1992.
Naftz, D. L., and Rice, J. A., "Geochemical Processes Controlling Selenium in Groundwater After Mining, Powder River Basin, Wyo., U.S.A.," *Appl. Geochem.,* 4:565–575, 1989.
Oremland, Ronald S. et al., "Measurement of in Situ Rates of Selenate Removal by Dissimilatory Bacterial Reduction in Sediments," *Environ. Sci. Technol.,* 24(8):1157–1164, 1990.
Oremland, Ronald S. et al., "Selenate Reduction of Elemental Selenium by Anaerobic Bacteria in Sediments and Culture: Biogeochemical Significance of a Novel, Sulfate-Independent Respiration," *Appl. Environ. Microbiol.,* 55(9):2333–2343, 1989.
Oremland, R. S. et al., "In situ Bacterial Selenate Reduction in the Agricultural Drainage Systems of Western Nevada," *Appl. Environ. Microbiol.,* 57:615–617, 1991.
Steinberg, Nisan A. et al., "Nitrate Is a Preferred Electron Acceptor for Growth of Freshwater Selenate-Respiring Bacteria," *Appl. Environ. Microbiol.,* 58(1):426–428, 1992.
Stackebrandt et al., "Proteobacteria Classes Nov., a Name for the Phylozenatic Taxon That Includes the " Purple Bacteria and Their Relatives, *Internat'l J of Systemic Bacteriology.,* 38(3):321–325, 1988.
92(4):21188 Energy Abstract of Dept of Energy Report. "Microbiol Treatment of Aqueous Wastes" by Lee et al. 1991.
Pauling, L. *College Chemistry* 3rd, Freeman, San Francisco, pp. 192–193. 1964.

(List continued on next page.)

*Primary Examiner*—Michael G. Wityshyn
*Assistant Examiner*—T. J. Reardon
*Attorney, Agent, or Firm*—Arnold, White & Durkee

[57] ABSTRACT

The invention relates to Proteobacteria that show unusually high level resistance to a wide range of metal oxides and oxyanions and to methods using selected subgroups for efficient reduction of certain metal oxides and oxyanions to the free metal. High level resistance was shown to be affected by growth conditions, and was observed in facultative photoheterotrophs such as *Rhodobacter sphaeroides* grown either chemoheterotrophically or photoheterotrophically.

26 Claims, 2 Drawing Sheets

FIGURE 1A

OTHER PUBLICATIONS

CA116(17):169869q Boone et al.

Chiong et al., "Purification and Biochemical Characterization of Tellurite-Reducing Activities from *Thermus thermophilus* HB8," J. Bacteriol., 170(7):3269–3273, 1988, published in U.S.A.

Gerrard et al., "Detection of Selenium Deposits in *Escherichia coli* by Electron Microscopy," J. Bacteriol., 119(3):1057–1060, 1974, published in U.S.A.

Goncharoff et al., "Structural, Molecular, and Genetic Analysis of the *kil*A Operon of Broad–Host–Range Plasmid RK2," J. Bacteriol., 173(11):3463–3477, 1991, published in U.S.A.

Jobling and Ritchie, "Genetic and physical analysis of plasmid genes expressing inducible resistance of tellurite in *Escherichia coli*" Mol. Gen. Gent., 208:288–293, 1987.

Jobling and Ritchie, "The nucleotide sequence of a plasmid determinant for resistance to tellurium anions," Gene, 66:245–258, 1988.

Kiffney and Knight, "The Toxicity and bioaccumulation of Selenate, Selenite and Seleno–L–Methionine in the Cyanobacterium *Anabaena flos-aquae*," Arch. Environ. Contam. Toxicol., 19:488–494, 1990.

Moore and Kaplan, "Identification and characterization of high–level resistance to tellurite, selenite and other rare–earth oxides in the facultative photoheterotroph, *Rhodobacter sphaeroides*," Abstracts of the 91st General Meeting of the American Society for Microbiology, K–128:235, 1991, published in U.S.A.

Rech and Macy, "Location of the Selenate Reducing Activity in a Selenate Respiring *Pseudomonas sp.*" Abstracts of the 91st General Meeting of the American Society for Microbiology, K–127:235, 1991, published in U.S.A.

Steinberg and Oremland, "Dissimilatory Selenate Reduction Potentials in a Diversity of Sediment Types," Applied and Environmental Microbiology, 56(11):3550–3557, 1990, published in U.S.A.

Summers and Jacoby, "Plasmid–Determined Resistance to Tellurium Compound," J. Bacteriol., 129:276–281, 1977, published in U.S.A.

Summers, "Microbial Transformation of Metals," Ann. Rev. Microbio., 32:637–672, 1978.

Taylor et al., "Structure and Location of Tellurium Deposited in *Escherichia coli* Cells Harboring Tellurite Resistance Plasmids," Journal of Ultrastructure and Molecular Structure Research, 99:18–26, 1988.

Tomas and Kay, "Tellurite Susceptibility and Non–Plasmid–Mediated Resistance in *Escherichia coli,*" Antimicrobial Agents and Chemotherapy, 30(1):127–131, 1986.

Walter and Taylor, "Comparison of Tellurite Resistance Determinants from the IncP$\alpha$ Plasmid RP4Te$^r$ and the IncHII Plasmid PHH1508a," J. Bacteriol., 171(4):2160–2165, 1989, published in U.S.A.

Walter et al., "Transcriptional Analysis, Translational Analysis, and Sequence of the *kil*A–Tellurite Resistance Region of Plasmid RK2Te$^r$," J. Bacteriol., 173(3):1111–1119, 1991, published in U.S.A.

Walter et al., "Two Different Mechanisms for Bacterial resistance to tellurite," Abstracts of the 91st General Meeting of the American Society for Microbiology, Q–270:321, 1991, published in U.S.A.

Walter and Taylor, "Plasmid–Mediated Resistance to tellurite: Expressed and Cryptic," Plasmid, 27:52–64, 1992.

BIOREDUCTION OF METAL OXIDES AND OXYANIONS BY PHOTOSYNTHETIC BACTERIA

The United States Government may have certain rights in the present invention pursuant to Grant Number GM15590 and Grant Number GM31667 awarded by the National Institutes of Health.

BACKGROUND OF THE INVENTION

1. Field of the Invention

The invention relates to microbiological methods of heavy-metal oxide or oxyanion removal from aqueous media by *Rhodobacter sphaeroides*. Several subgenera of Rhodobacter and related species efficiently reduce the metal oxides and oxyanions of selenium, tellurium and rhodium to the free metal which is readily isolated from the cytoplasmic membrane. These microorganisms exhibit resistance to a wide variety of oxides and oxyanions making bioremediation of selected heavy-metal oxides and oxyanions feasible, even in the presence of other oxides and/or oxyanions including those of vanadium, iodine, silicon, molybdenum, tin, tungsten, antimony and arsenic.

2. Description of Related Art

A major environmental problem exists in dealing with toxic metal compounds found ubiquitously dispersed in groundwater, lakes, plant effluents, and aqueous waste. Generally these toxic compounds are heavy metal oxides or oxyanions exemplified by the tellurite, arsenate and periodate classes of rare-earth oxyanions and oxides. A particularly obnoxious group of contaminants identified as a threat to western United States water supplies includes the oxyanions of selenium frequently found in agricultural wastewaters (Sylvester, 1988).

Potential and actual health problems also arise due to toxic effects of many oxidized heavy metals. Exposure to tellurium compounds is hazardous to workers in the film and rubber industries, as well in battery manufacture. When accumulated in the human body, many of these elements have detrimental mental and physical effects (Schroeder et al., 1967).

Bioremediation has been explored as a method of detoxification of toxic compounds found in water. Proposed methods generally take advantage of microbiological resistance to such compounds. The basis of resistance may be metabolic breakdown or concentration of the material within the microorganism. It is known, for example, that some species of Gram-positive bacteria, such as *Corynebacterium diphtheriae, Streptococcus faecalis* and most strains of *Staphylococcus aureus* are naturally resistant to tellurite and will often concentrate metallic tellurium inside the inner membrane (Walter and Taylor, 1989). Resistance determinants to tellurite have been identified and isolated in *Escherichia coli* (Walter and Taylor, 1989). However, resistance to tellurite is not a common property of bacteria and examples of naturally-occurring resistant strains are rare (Chiong et al., 1988). Often times such resistance is to only low or moderate levels of these compounds, e.g. $\leq 100$ $\mu$g/ml.

A method for accelerating recovery of selenium from aqueous streams is based on bioreduction of Se(VI) to Se(IV) with strains of the soil bacterium, Clostridium. A rapid exchange reaction between selenous acid and pyrite is used to remove the selenium from solution. However, to remove selenium, further processing is required, e.g., generation of hydrogen selenide and subsequent oxidization to the free metal (Khalafalla, 1990). Clostridium species have also been utilized in a process for reducing waste-containing radionuclides or toxic metals, but the process requires obligate anaerobic conditions at elevated temperatures (Francis and Gillow, 1991).

In addition to bioremediation, microorganisms are thought to have practical value in possible reclamation of metals from such sources as low grade ores, or in recovery processing. However, while a few bacterial species have resistance to one or more metal cations under some conditions, resistance may be based on accumulation rather than a metabolic reaction. Few microorganisms have been identified that reduce metal cations to the free metal (Summers and Silver, 1978). Moreover, resistance may not be to whole classes of such compounds, but to only a few.

SUMMARY OF THE INVENTION

The present invention addresses one or more of the foregoing problems in providing a method to effectively bioreduce oxidized metals present in aqueous media. Under certain conditions, some members of the subgenera *Rhodobacter sphaeroides* will reduce oxyanions and oxides of selenium, tellurium and rhodium to the free metal. The microorganisms survive in the presence of high levels of a wide variety of metal oxides and oxyanions, including those of arsenic, tungsten, tin, sulfur, antimony, silicon and vanadium. The invention also includes a strain of *Rhodobacter sphaeroides* particularly effective in reducing oxyanions of tellurium to the free metal when the microorganism is grown under photoheterotrophic conditions, allowing isolation of a cell fraction containing free metal. In this respect, efficient deposition of free metal occurs in the cytoplasmic membrane, but not the photosynthetic membrane. *Rhodobacter sphaeroides* will also accomplish the same reactions under chemoheterotrophic growth conditions.

The method of the present invention involves the use of the photosynthetic Proteobacteria. Proteobacteria is the generally accepted class designation for the phylogenetic taxon that includes purple bacteria and their relatives. The group is a diverse but related group of gram-negative bacteria including phototrophic and heterotrophic bacteria (Stackebrandt, et al., 1988). In one aspect of the invention the bacterium is useful for reducing oxidized metals in aqueous media. Metal oxides or metal oxyanions in a aqueous sample are contacted with particular members of the photosynthetic Proteobacteria which are grown under conditions that allow reduction of the oxidized metal. The species of Proteobacteria most useful in the practice of this invention are *Rhodobacter sphaeroides* or *Rhodobacter capsulatus*. Preferred strains include *R. sphaeroides* 2.4.1, 2.4.7, RS2, and WS8, and *R. capsulatus* B10. Most preferred are strains 2.4.1 and 2.4.1$\Delta$S of *R. sphaeroides*. There are other Proteobacteria (including members of the $\alpha$-2 and $\alpha$-3 phylogenetic subgroups) able to reduce metal oxides and metal oxyanions in aqueous solution. However, high-level resistance (HLR) to certain metal oxyanions has not been found in members of the $\alpha$-1, $\beta$-1 and $\gamma$-3 subgroups.

High level resistance of *R. sphaeroides*, particularly strain 2.4.1, has been shown with several classes of oxyanions, including the "tellurite class" of oxyanions. Typical oxyanions of this class include, for example, tellurate, tellurite, selenate, selenite and rhodium sesquioxide. Reduction of oxyanions in this class results in deposition of the pure metal, for example, metallic selenium, tellurium or rhodium in the cytoplasmic membrane of the microorganism employed.

Reduction of metal oxides or metal oxyanions from aqueous solutions in the presence of a bacterium such as *R. sphaeroides* is most preferably conducted under either aerobic or anaerobic conditions. Under aerobic conditions both *R. sphaeroides* and *R. capsulatus* express intrinsic HLR to tellurite with minimum inhibitory concentrations at least 80 times higher than minimum inhibitory concentrations previously described for *E. coli*, an enteric member of the γ-3 phylogenetic subgroup. *Rhodopseudomonas palustris* is an α-2 species. This microorganism expresses intrinsic resistance to tellurate that is 40 times greater than *E. coli*, while two photosynthetic members of the α-1 group and β-1 subgroups *Rhodospirillum rubrum* and *Rhodocyclus gelatinosus* show low resistance to tellurite.

Generally, intrinsic high-level resistance to metal oxides and/or metal oxyanions appears to occur in a number of species of purple non-sulphur bacteria during aerobic and anaerobic growth conditions. Moreover, the level of tellurite resistance appears to be strain-dependent. Minimum inhibitory concentration (MIC) for *R. sphaeroides* RS2 is approximately two- to three-fold lower than the MIC for either strain 2.4.1, 2.4.7, or WS8. Generally, MICs are approximately 50% higher when cells are grown aerobically regardless of the strain or species, although one exception, *R. gelatinosus* has been found where there are no growth dependent differences in inhibitory metal oxyanion concentration, at least for tellurite.

Unexpectedly, composition of the medium in which the microorganism is grown has a significant effect on the resistance level of the microorganism to metal oxides or metal oxyanions in aqueous solution. For example, rich media such as Luria-Bertani, yeast extract/peptone, or proteose-peptone medium are not conducive to high-level resistance. When grown in these media, *R. sphaeroides* 2.4.1 is sensitive to relatively low levels of the oxyanion. This is true whether or not the cultures are grown aerobically or anaerobically. A preferred medium is a minimal medium such as Sistrom's minimal medium A, ATCC medium 530, or Ormerod's photosynthetic minimal medium. High-level resistance to metal oxides or metal oxyanions decreases drastically when the medium is supplemented with peptone, casamino acids, tryprone or yeast extract. Surprisingly, there is strong evidence that inhibition of high-level resistance is due solely to the presence of a single amino acid, L-cysteine. Other compounds such as other amino acids or alternate electron acceptors such as trimethylamine-N-oxide or dimethyl sulfoxide (DMSO) do not appear to affect high-level resistance when added to minimal medium. With this knowledge, it is possible to eliminate the effect of L-cysteine and its inhibitory properties either by removing or destroying the L-cysteine, or by isolation of mutant strains unaffected by the L-cysteine.

Alternatively, and in addition to aerobic conditions in minimal medium, wild-type *R. sphaeroides* strains may be cultured anaerobically, either photosynthetically or employing anaerobic respiration. In preferred embodiments for the reduction of tellurite to tellurium metal, resistance in photosynthetically-grown cultures is directly proportional to incident light intensity. A preferred light intensity is $10W/m^2$ which allows MICs at least two-fold higher than for cultures grown at $3W/m^2$. It is likely that optimal conditions in terms of light intensity should be developed for each metal desirous of being reduced. While $10W/m^2$ has been found useful for the reduction of tellurite, other optimal light conditions combined with appropriate culture medium may result in even higher MICs of tellurite as well as for other heavy-metal oxides and oxyanions. In practical terms, sunlight would probably be the preferred method of providing conditions conducive to encouraging high-level resistance in the photosynthetic bacteria.

*Rhodobacter sphaeroides* 2.4.1 and other photosynthetic proteobacteria may be grown by a variety of methods including aerobically (in shaking flasks, for example, or by sparging large liquid cultures with oxygen); anaerobically, either photosynthetically (in the presence of light using organic acids or carbon dioxide as a carbon source) or in the absence of light (with the addition of an alternate electron acceptor such as DMSO or TMAO to the growth medium), or by fermentation of organic compounds such as pyruvate. They may also be grown photosynthetically in the presence of hydrogen and carbon dioxide. These organisms can also be grown employing nitrogen gas as the sole nitrogen source.

The invention also includes a means of facilitatina high-level resistance of a photosynthetic proteobacterium to metal oxides and oxyanions. Proteobacteria are grown aerobically in minimal medium preferably having a carbon source that has a low oxidation state. As used in this context, low oxidation. State refers to carbon compounds that are highly reduced. A highly preferred carbon source is a dicarboxylic acid such as malate or succinate, or a monocarboxylic acid such as butyrate. There are numerous other low oxidation state carbon sources that may be used such as other organic acids and alcohols.

When grown in minimal medium having a carbon source in a low oxidation state, strains of *R. sphaeroides* exhibit high-level resistance to a wide variety of metal oxides and oxyanions including silicon, molybendum, arsenic, tungsten, tin, sulphur, antimony, or vanadium. *R. sphaeroides* 2.4.1 in particular shows resistance to the oxides $MoO_3$, $NH_4VO_3$, $Rh_2O.5H_2O$, $Sb_2O_3$, and $SnO_2$. Other oxyanions to which resistance was shown include $IO_4$, $SiO_3^{2-}$, and $SiO_4^{2-}$, as well as arsenate, molybdate, stannate, sulphite and tungstate.

A mutant photosynthetically competent strain of *R. sphaeroides* 2.4.1ΔS genotype is also part of the present invention. *R. sphaeroides* 2.4.1 Δs is a derivative of *R. sphaeroides* 2.4.1 which has been "cured" of one of its five endogenous plasmids, the 42 kb plasmid designed e (Fornari et al., 1984) or "S" factor (Suwanto and Kaplan, 1989A; Suwanto and Kaplan, 1989B; Suwanto and Kaplan, 1991). The plasmid is readily cured as described in Suwanto and Kaplan by the introduction of either of the incompatibility determinants, IncA or IncB derived from native "S" factor on a selectable antibiotic resistance containing, unstable plasmid derivative. Once "S" is cured, the introduced plasmid is readily lost following removal of the antibiotic selection. Two important features of 2.4.1Δs are that the phenotype associated with oxyanion or metal oxide metabolism is not associated with the "S" factor and that this strain may be used in conjugal genetic studies involving oriT mediated chromosome transfer.

Numerous genetic manipulations of *R. sphaeroides* are envisioned. Photosynthetic proteobacteria may be genetically engineered to provide to the oxyanion and metal oxide metabolic properties associated with *R. sphaeroides* 2.4.1. genotypes.

Yet another aspect of the present invention is metal purification utilizing *R. sphaeroides*. Generally, *R. sphaeroides* is cultured either under photoheterotrophic or chemoheterotrophic growth conditions, generally described herein above. A sample containing a metal oxide or oxyanion is added, followed by isolation of a cell fraction containing the free metal.

Photoheterotrophic and chemoheterotrophic conditions for growing *R. sphaeroides* are described herein and may be varied somewhat depending on the particular strain of *R. sphaeroides* employed. While the method is not limited to *R. sphaeroides* and may utilize any photosynthetic bacterium that shows high-level resistance, strains 2.4.1 and 2.4.1ΔS have demonstrated particularly high-level resistance to tellurite and are most preferred for reduction of tellurite to the free metal and subsequent isolation.

Metals isolated by the described method are typically localized in the cytoplasmic membrane. Isolation is readily accomplished by centrifugation and most preferably by sucrose density gradient centrifugation. The method works particularly well for metals such as selenium, tellurium, rhodium and the like. The method is further contemplated to be useful for the isolation of such elements as gold, platinum, palladium, silver, titanium, iridium, germanium, plutonium, uranium, and the like, from their oxides, and oxyanion states.

Metal oxides or metal oxyanions reduced by this method appear to be located in a particular subcellular region, namely the cytoplasmic membrane. When shear forces are applied to such, as in a sucrose density gradient, the cytoplasmic membrane may be cleanly separated from other cellular constituents, including the photosynthetic membrane. This allows purification of the metal-laden cytoplasmic membrane and isolation of the free metal.

DETAILED DESCRIPTION OF THE PREFERRED EMBODIMENTS

Figure 1A:
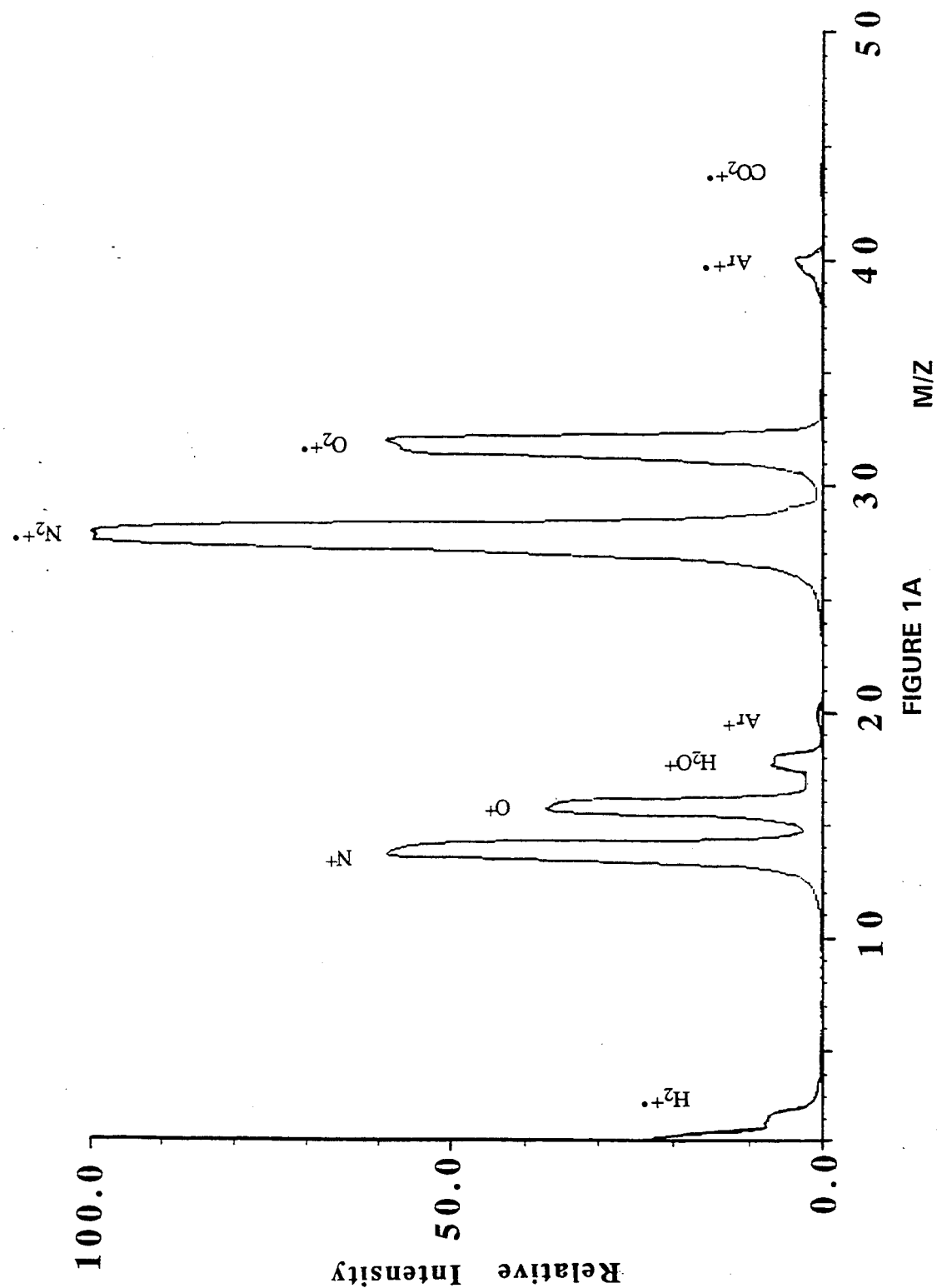
FIG. 1A is the mass spectrum of the headspace gas collected above photosynthetic (10 W/m² incident light intensity) cultures of *R. sphaeroides* grown in the absence of 250/µg/ml $K_2TeO_3$.

The invention generally relates to proteobacteria having the ability under certain conditions to efficiently reduce metal oxides and oxyanions to the free metal, and to their ability to survive in the presence of a wide range of metal oxides and oxyanions. The several examples following illustrate free metal deposition in a species of *R. sphaeroides* and its growth in the presence of toxic metal oxides and oxyanions. Selective growth conditions conducive to high level resistance of the microorganisms are also described.

The following examples are intended to illustrate the practice of the present invention and are not intended to be limiting. Numerous variations of growth conditions are envisioned which are expected to optimize for different metal oxides and oxyanions. It is also expected that one or more resistance factors, plasmid or chromosomal, identified with resistance will be isolated and sequenced, providing cassettes for transforming various host cells.

EXAMPLE 1

This example illustrates the intrinsic resistance of several species of Proteobacteria to tellurite. Intrinsic high-level resistance to tellurite is found in only a few species of these purple non-sulfur bacteria during chemoheterotrophic, anaerobic/dark, and photoheterotrophic growth conditions.

$TeO_3^{2-}$ Resistance in Proteobacteria

Several wild-type strains were grown either aerobically, anaerobically in the dark, or photoheterotrophically in minimal media in the presence of $TeO_3^{2-}$. Table 1 lists the bacterial strains tested for high level resistance to tellurite.

TABLE 1

| Organism/strain | Bacterial strains. Relevant genotype/phenotype[a] | Reference |
|---|---|---|
| *Escherichia coli* | | |
| JM83 | ara, Δ(lac-proAB), rpsL, thi, φ80dlacZ ΔM15 | Messing, 1979 |
| S17-1 | C600::RP-4, 2-Tc::Mu::Km::Tn7 hsdR, hsdM+, recA | Simon, et al., 1983 |
| *Rhodobacter capsulatus* | | |
| B10 | Wild-type | Weaver, et al., 1975 |
| *Rhodobacter sphaeroides* | | |
| 2.4.1 | Wild-type, 5 endogenous plasmids | |
| 2.4.1ΔS | 2.4.1Δ(42-kb plasmid) | Suwanto |
| 2.4.1-Ga | Car⁻ | Cohen-Bazire, 1956 |
| 2.4.7 | Wild-type, 2 endogenous plasmids | |
| BC17 | 2.4.1-ga, fbcBC, Car⁻, Km$^r$ | Yun, 1990 |
| CFXA⁻ | cfxA, Km$^r$ | Hallenbeck, et al., 1990A |
| CFXB⁻ | cfxB, Sp$^r$, Sm$^r$ | Hallenbeck, et al., 1990A |
| CFXA⁻B⁻ | cfxA, cfxB, Km$^r$, Sp$^r$, Sm$^r$ | Hallenbeck, et |

TABLE 1-continued

Bacterial strains.

| Organism/strain | Relevant genotype/phenotype[a] | Reference |
|---|---|---|
| | | al., 1990A |
| CYCA1 | cycA, Km[r] | Donohue, 1988 |
| MM1004 | 2.4.1::TnphoA, DORase[−], Km[r] | Moore and Kaplan, 1989 |
| MM1006 | 2.4.1::TnphoA, Bchl[−], Km[r] | Moore and Kaplan, 1989 |
| PRKA[−] | prkA, Km[r] | Hallenbeck, et al., 1990B |
| PRKB[−] | prkB, Sp[r], Sm[r] | Hallenbeck, et al., 1990B |
| PRKA[−]B[−] | prkA, prkB, Km[r], Sp[r], Sm[r] | Hallenbeck, et al., 1990B |
| PUC705-BA | pucBA, Km[r] | Lee, 1989 |
| PUFB1 | pufBALMX, Km[r] | Davis, 1988 |
| PUHA1 | puhA, Km[r] | Sockett, 1988 |
| RS2 | Wild-type | Meinhardt, 1985 |
| WS8 | Wild-type, 1 endogenous plasmid | Sistrom, 1977 |
| *Rhodocyclus gelatinosus* | | |
| str-1 | Wild-type | Uffen, 1976 |
| *Rhodopseudomonas palustris* | | |
| 1e5 | Wild-type | Firsow, 1977 |
| *Rhodopseudomonas viridis* | | |
| F | Wild-type | Drews, 1966 |
| *Rhodospirillum rubrum* | | |
| Ha | Wild-type | |

[a]Km[r], Sp[r], and Sm[r] denote resistance to kanamycin, spectinomycin, and streptomycin, respectively.

All Proteobacteria were grown at 30° C. with the exception of *E. coli* which was cultured at 37° C. on a Gyrotary shaker. Cultures of *R. sphaeroides* and *R. gelatinosus* were grown in LB, YP, or SMM containing either 0.4% succinate, 0.4% malate, or 0.4% butyrate as a carbon source. Cultures of *R. capsulatus* were grown in RCVB minimal medium containing 0.4% malate as a carbon source; *R. rubrum* was grown in SMM containing 0.4% malate, and 0.1% yeast extract. *R. palustris* and *R. viridis* were grown in SMM containing 0.4% malate, 0.1% yeast extract, and 50 μg/ml each of p-aminobenzoic acid and cyanocobalamin. When necessary, antibiotics were added to growth media at the following final concentrations: kanamycin (Km), 25 μg/ml; spectinomycin (Sp), 50 μg/ml; and streptomycin (Sm), 50 μg/ml. Anaerobic-dark growth of *R. sphaeroides* on SMM medium containing DMSO, and photoheterotrophic growth conditions have been previously reported.

Under aerobic conditions, both *R. sphaeroides* and *R. capsulatus* expressed intrinsic high level resistance to $TeO_3^{2-}$ while virtually all other strains of bacteria tested showed much lower resistance under the same culture conditions. Results are shown in Table 2.

As indicated in Table 2, intrinsic high level resistance to tellurite occurred in only a few species of purple non-sulfur bacteria during aerobic and photoheterotrophic growth conditions. Moreover, the level of tellurite resistance was strain dependent: the MIC of $K_2TeO_3$ for *R. sphaeroides* RS2 was approximately two- to three fold lower than the MIC for either strain 2.4.1, 2.4.7 or WS8. With the exception of *R. gelatinosus*, which exhibited no growth dependent difference in inhibitory $TeO_3^{2-}$ concentration, MICs were approximately 50% higher when cells were grown

TABLE 2

Determination of intrinsic HLR to $TeO_3^{2-}$ by Proteobacteria.

| Organism | Strain | Phylogenetic[a] subgroup | MIC $K_2TeO_3$ (μg/ml)[b] Aerobic | Photosynthetic[c] |
|---|---|---|---|---|
| *Rhodospirillum rubrum* | Ha | α-1 | 20 | 10 |
| *Rhodopseudomonas palustris* | 1e5 | α-2 | 200 | 100 |
| *Rhodopseudomonas viridis* | F | α-2 | 80 | 50 |
| *Rhodobacter sphaeroides* | 2.4.1 | α-3 | 900 | 600 |
| | WS8 | α-3 | 800 | 600 |
| | 2.4.7 | α-3 | 800 | 500 |
| | RS2 | α-3 | 400 | 250 |
| *Rhodobacter capsulatus* | B10 | α-3 | 800 | 500 |
| *Rhodocyclus gelatinosus* | str-1 | β-1 | 5 | 10 |
| *Escherichia coli* | JM83 | γ-3 | <5 | NA[d] |
| | S17-1 | γ-3 | <5 | NA |

[a]Based on the classification of Woese et al.
[b]MICs were determined in the appropriate minimal synthetic medium at 30° C.
[c]Incident light intensity, 10 W/m².
[d]NA, not applicable.

aerobically, regardless of the strain or species. The JM83 and S17-1 strains of *E. coli* failed to grow in minimal medium containing 5 μg/ml $K_2TeO_3$.

EXAMPLE 2

The ability of *R. sphaeroides* to grow in the presence of selenium, tellurium and rhodium oxyanions is demonstrated in the following example.

Growth of R. sphaeroides in the Presence of Te, Se or Rh-Containing Oxyanions Cells of *R. sphaeroides* 2.4.1 were grown in liquid medium as in Example 1 When medium contained $TeO_3$ or $TeO_4^{2-}$, cells settled to the bottom of culture tubes over the course of the growth phase due to the intracellular accumulation of a dense metal deposit. Copious gas evolution was observed concomitant with cell growth. Centrifugation of broth cultures at $10000 \times g$ resulted in a black cell pellet and a clear supernatant. Colonies of *R. sphaeroides* which formed on agar medium containing $TeO_3^{2-}$ produced a black deposit which did not diffuse into the medium. Cells remained viable despite the accumulation of intracellular deposits: black colonies streaked onto agar medium containing no $TeO_3^{2-}$ gave rise to normally pigmented colonies apparently through the dilution of metal complexes in the membranes of progeny cells.

Similar results were obtained for selenium and rhodium containing compounds: when culture media contained $SeO_3^{2-}$ or $SeO_4^{2-}$, the cells became bright red in color; in rhodium sesquioxide-containing media, the cells appeared grayish bronze. The relative toxicity of these five compounds to *R. sphaeroides* was $SeO_4^{2-} > TeO_4^{2-} > TeO_3^{2-} > SeO_3^{2-} > Rh_2O_3 \cdot 5H_2O$.

EXAMPLE 3

The effect of culture conditions and medium composition on the high-level resistance of *R. sphaeroides* to heavy-metal oxides was examined. Significant differences in resistance were found depending on the nature of the carbon source, incident light intensity and the presence of oxygen.

Effect of Culture Conditions and Medium Composition on High Level Resistance to $TeO_3^{2-}$

*R. sphaeroides* 2.4.1 was grown either in complex or defined medium as indicated in Table 3.

While cultures of *R. sphaeroides* 2.4.1 grown in SMM expressed HLR to $TeO_3^{2-}$, cells grown in rich media such as LB, YP or proteose-peptone were sensitive to very low levels of the oxyanion, Table 3. This was true for cultures grown aerobically or anaerobically. Likewise, a thirty- to forty-fold reduction in $TeO_3^{2-}$ resistance was observed when SMM was supplemented with either peptone, Casamino acids, tryptone, or yeast extract. To determine if there was a single common component present in these supplements which was affecting HLR, SMM containing 0.4% succinate was supplemented individually with each of the twenty amino acids. This analysis indicated that a single amino acid, L-cysteine, was solely responsible for the increased sensitivity to $TeO_3^{2-}$. Neither cystine, glutathione nor thioglycollate, however, decreased HLR to $TeO_3^{2-}$ when added to SMM, nor did the presence of alternate electron acceptors, such as trimethylamine-N-oxide or DMSO, Table 3. The fact that the addition of L-methionine to SMM had no affect on HLR to $TeO_3^{2-}$ contrasted with previously studies with *E. coli* which demonstrated that exogenously supplied L-methionine enhanced $TeO_3^2$ resistance some two-fold (Scala and Williams, 1962; 1963). A similar inhibition of HLR by L-cysteine was also observed for $TeO_4^{2-}$, $SeO_3^{2-}$, and $SeO_4^{2-}$. Likewise, HLR to none of these compounds was enhanced by the addition of exogenous methionine.

TABLE 3

Effects of medium composition and growth conditions on HLR to $TeO_3^{2-}$.

| | | MIC $K_2TeO_3$ (μg/ml) | | | |
|---|---|---|---|---|---|
| | | | Photosynthetic | | Anaerobic- |
| Medium[a] | Supplement[b] | Aerobic | 10 W/m² | 3 W/m² | dark[d] |
| Complex: | | | | | |
| Luria-Bertani | — | 20 | 80 | 40 | <10 |
| Yeast Extract/Peptone | — | 20 | 20 | 10 | <10 |
| Proteose-peptone | — | 10 | 20 | 10 | 10 |
| Defined: | | | | | |
| SMM + Butyrate | — | 1000 | 700 | 500 | 200 |
| SMM + Succinate | — | 900 | 600 | 300 | 150 |
| SMM + Malate | — | 800 | 400 | 150 | 100 |
| SMM + Succinate | 30 mM TMAO | 850 | 650 | 400 | 150 |
| SMM + Succinate | 1 mM L-Methionine | 800 | 500 | 200 | 100 |
| SMM + Succinate | 1 mM Cystine | 500 | 550 | 200 | 100 |
| SMM + Succinate | 1 mM Glutathione | 550 | 550 | 250 | 150 |
| SMM + Succinate | 1 mM Thioglycollate | 500 | 500 | 250 | 100 |
| SMM + Succinate | 0.3% Peptone | 30 | 20 | 20 | 20 |
| SMM + Succinate | 0.3% Yeast Extract | 30 | 40 | 10 | 10 |
| SMM + Succinate | 0.3% Tryptone | 20 | 30 | 10 | 20 |
| SMM + Succinate | 0.3% Casamino Acids | 20 | 30 | 10 | 20 |
| SMM + Succinate | 1 mM L-Cysteine | 20 | 40 | 20 | 10 |

[a]SMM contained 0.4% of the carbon source listed.
[b]Supplement was added to culture medium to the final concentration listed.
[c]Incident light intensity.
[d]Supplemented with 60 mM DMSO.

Regardless of medium composition, the MIC of $K_2TeO_3$ for *R. sphaeroides* 2.4.1 was always two- to three-fold higher in aerobically- vs. photosynthetically-grown cultures. This was consistent with results obtained earlier for cells grown in succinate-containing SMM (Table 2). Analyses also demonstrated that HLR to $TeO_3^{2-}$ in photosynthetically-grown cultures was directly proportional to incident light intensity; in all the growth media examined, MICs were at least two-fold higher for cultures grown at 10 W/m² than for those grown at 3 W/m², see Table 3.

A final observation with respect to medium composition concerned the effect the oxidation state of the carbon source had on the level of $TeO_3^{2-}$ resistance in *R. sphaeroides* 2.4.1. While the MIC of $K_2TeO_3$ for cells grown aerobically in SMM containing malate as the carbon source was 800 μg/ml, when more reduced carbon sources such as succinate or butyrate were substituted the MICs increased to 900, and 1000 μg/ml, respectively. Similar results were also observed when cells were grown anaerobically in the light (photosynthetically) or anaerobically in the dark (in SMM containing DMSO), see Table 3. These data suggested that the toxicity of $TeO_3^{2-}$ was inversely related to the oxidation state of the carbon source: the more reduced the carbon source, the higher the MIC of $TeO_3^{2-}$.

EXAMPLE 4

This example illustrates the remarkable resistance of R. sphaeroides to a wide variety of oxides and oxyanions. The example is illustrated with strain 2.4.1 but similar resistance has been obtained with related strains such as Rhodobacter sphaeroides 2.4.1As, 2.4.7, WS8, RS2, 2.4.1-Ga; Rhodobacter capsulatus B10; Rhodopseudomonas palustris 1e5; Rhodopseudomonas viridis F.

Mutant R. sphaeroides having intrinsic high level resistance to oxides and oxyanions have been deposited with the American Type Culture Collection, 12301 Parklawn Drive, Rockville, Md. 20852 under the Budapest Treaty on the International Recognition of the Deposit of Microorganisms for the Purposes of Patent Procedure. All restrictions on the availability to the public of the material so deposited are irrevocably removed upon the granting of a patent. ATCC designations for the deposits are: ATCC 49848 (R. sphaeroides 2.4.1ΔS), deposited on Jan. 24, 1992, ATCC 55398 (R. sphaeroides 2.4.1), deposited on Mar. 9, 1993,; ATCC 17028 (R. sphaeroides 2.4.7), deposited on Feb. 12, 1965,; and ATCC 33303 (Rhodobacter capsulatus B10), deposited on Feb. 26, 1987.

A preferred strain used in some of the examples of the invention is Rhodobacter sphaeroides 2.4.1. This strain differs from the American Type Culture Collection strains (ATCC 17023, ATCC 11167, ATCC 14690, NCIB 8253 and NCIB827) which are also named as 2.4.1. The 2.4.1 strain used herein was originally provided by Dr. W. R. Sistrom over 20 years ago. It is believed that he received this strain from the laboratory of Dr. R. Y. Stanier, who in turn received it from Dr. C. B. vanNiel. It is unclear how the discrepancies in nomenclature between the 2.4.1 strain obtained from Dr. Sistrom and the ATCC strains arose.

The Rhodobacter sphaeroides 2.4.1 used herein may be obtained from Dr. Samuel Kaplan, The University of Health Science Center at Houston, Department of Microbiology and Molecular Genetics, P.O. Box 20708, Houston, Tex., USA 77225. An equally preferred strain is Rhodobacter sphaeroides 2.4.1Δs, which has ben deposited with the American Type Culture Collection, Rockville, Md. 20852.

Strains of Rhodobacter are readily isolated from soil or pond water samples. Strain WS8, like other strains of Rhodobacter, may be readily identified as an R. sphaeroides related strain on the basis of the following properties. The cells are very short, small, gram-negative, motile rods, frequently occurring in pairs but seldom in longer chains. Gelatin is not liquified; growth is vigorous on lactate, realate or glucose, less vigorous on mannitol, tartrate, or propionate, and absent on glycerol or citrate; anaerobic (phototropic) cultures are brownish yellow; semi-aerobic cultures are reddish-orange. Except for the lack of growth on glycerol, these are characteristics of R. sphaeroides.

Additionally, other strains of photosynthetic proteobacteria exist which are likely to effect for metaloxide and oxyanion reduction, for example, other strains of R. sphaeroides commonly referred to as "2.4.1" (e.g., ATCC 11167, ATCC 14690, ATCC 17023, NCIB 8253, and NCIB 8287) that, while genetically distinct from 2.4.1 should be expected to carry out oxide and oxyanion reduction in a manner similar to 2.4.1.

Multiple-Oxyanion High-Level Resistance in R. sphaeroides 2.4.1

A total of twenty oxides and oxyanions were assayed for toxicity to R. sphaeroides 2.4.1. Results are shown in Table 4.

Twenty oxides and oxyanions, listed in Table 4, were assayed for toxicity to R. sphaeroides 2.4.1. Of those examined, only $CrO_3$, $CrO_4^{2-}$, and $MnO_4^-$ had MICs<20 μg/ml; the others had MICs in SMM>100 μg/ml under all growth conditions examined. Oxides having limited solubilities in SMM (e.g., $MoO_3$, $NH_4VO_3$, $Rh_2O_3.5H_2O$, $Sb_2O_3$, and $SnO_2$) did not affect cell growth when present in growth media as satu-

TABLE 4

| | | | Quantitation of oxide and oxyanion resistance in R. sphaeroides 2.4.1. | |
|---|---|---|---|---|
| | Intracellular | Gas | MIC (μg/ml)[a] | |
| Compound | deposition | evolution | Standard Medium | Low-$PO_4^{3-}$ Medium[c] |
| $MoO_3$ | — | — | sat'd sol'n[b] | sat'd sol'n |
| $NH_4VO_3$ | — | — | sat'd sol'n | sat'd sol'n |
| $Sb_2O_3$ | — | — | sat'd sol'n | sat,d sol'n |
| $SnO_2$ | — | — | sat'd sol'n | sat'd sol'n |
| $Rh_2O_3.5H_2O$ | +++ | +++ | sat'd sol'n | sat'd sol'n |
| $Na_2SeO_4$ | ++ | + | 150 | 100 |
| $Na_2SeO_3$ | ++++ | +++ | 800 | 500 |
| $K_2TeO_4$ | +++ | ++ | 500 | 500 |
| $K_2TeO_3$ | ++++ | ++++ | 600 | 600 |
| $NaSiO_4$ | — | — | 400 | 150 |
| $Na_2SiO_3$ | — | — | 400 | 100 |
| $Na_2SiO_4$ | — | — | 300 | 100 |
| $Na_2HAsO_4$ | — | — | 1500 | 1600 |
| $Na_2MoO_4$ | — | — | 1400 | 1500 |
| $Na_2WO_4$ | — | — | 1600 | 1600 |
| $Na_2SnO_4$ | — | — | 800 | 800 |
| $Na_2SO_3$ | — | — | 600 | 500 |
| $Na_2CrO_4$ | — | — | 10 | 20 |
| $KMnO_4$ | — | — | 20 | <10 |
| $CrO_3$ | — | — | 20 | <10 |

[a]Photoheterotrophic growth in SMM containing succinate (10 W/m² incident light intensity.
[b]Compounds with solubilities <10 μg/ml did not inhibit growth in saturated solution.
[c]Medium contains 2 mM $PO_4^{3-}$, 10-fold lower than that of the standard formulation.

rated solutions. Only cultures grown in the presence of Te-, Se-, or Rh-containing oxyanions evolved gas and accumulated intracellular deposits, Table 4. HLR to these five compounds was unaffected by extracellular $PO_4^{3-}$, which suggested HLR to these compounds in *R. sphaeroides* 2.4.1 was not mediated by components of the phosphate-transport system. This would preclude any similarity between the mechanism of intrinsic HLR in *R. sphaeroides* and that encoded by the IncPα plasmid determinants, telA and telB (Walter et al., 1991).

*R. sphaeroides* was also highly resistant to a second class of oxyanions, the "periodate class", but the resistance mechanism to this class differed significantly from that of the "tellurite class." Neither $IO_4^-$, $SiO_3^{2-}$, nor $SiO_2^{4-}$ was reduced to its elemental state, and no gas evolution was observed. In sharp contrast to the "tellurite class," resistance to these oxyanions decreased three- to four-fold when the extracellular phosphate was reduced ten-fold. This suggested that resistance in *R. sphaeroides* 2.4.1 occurred as a result of reduced transport or increased efflux via a phosphate-transport system-mediated mechanism. It is interesting to note, however, that intrinsic resistance to these compounds in *R. sphaeroides* was still some twenty-fold greater than that of the γ-3 Proteobacteria (Summers and Silver, 1978).

A third class of oxyanions to which *R. sphaeroides* was highly resistant, the "arsenate class," was also examined. This group included arsenate, molybdate, stannate, sulfite, and tungstate. Similar to the "tellurite class" oxyanions, resistance to these compounds was unaffected by extracellular phosphate levels. In contrast, however, HLR to "arsenate class" compounds did not result in oxyanion reduction or intracellular metal sequestration. Like the "periodate class" oxyanions, these compounds were not reduced to their elemental states, and no gas was evolved. These data supported the existence of a third and distinctly different mechanism to effect HLR to "arsenate-class" oxyanions.

EXAMPLE 5

The ability of *R. sphaeroides* to concentrate tellurium metal in the cytoplasmic membrane is shown in this example. The dense metal deposit was shown to be localized to the cytoplasmic membrane after a sucrose gradient isolation, leaving the intracytoplasmic (or photosynthetic) membrane unaffected.

Isolation of Tellurium from Membrane Fractions of *R. sphaeroides* 2.4.1

Two one-liter cultures of *R. sphaeroides* 2.4.1 were grown photoheterotrophically (10 W/m² incident light intensity) in SMM containing 0.4% succinate to a cell density of approximately 1.5 $1.5 \times 10^9$ cells/ml. Prior to inoculation one flask was supplemented with 275 mg $K_2TeO_3$ (equivalent to 138.3 mg $Te^{IV}$) to give a final medium concentration of 250 μg/ml $K_2TeO_3$. Following subcellular fractionation, the dense black deposit which accumulated within cells grown in $TeO_3^{2-}$-containing medium was localized to the cytoplasmic membrane via centrifugation through a discontinuous sucrose gradient. No metallic material was observed in the enriched chromatophore fraction (consisting of photosynthetic or intracytoplasmic membrane) at the 20:40% interface.

850 mg of crude membrane-metal complex was isolated. After purification and extraction with acetone:-methanol and ethanol, 203 mg of a finely-divided metallic material resulted. Analysis of a 50.4 mg sample of this material identified 23.2 mg of $Te^o$ (a minimum net purity of 46%). The minimum $Te^o$ deposited in the one-liter culture, therefore, was 93 mg (203 mg×0.46) or 0.7333 mmole. Since the growth medium initially contained 138.3 mg of $Te^{IV}$, a minimum $Te^{IV}$ to $Te^o$ conversion of 67% was obtained.

Assay of the membrane fraction of cells grown in the absence of $TeO_3^{2-}$ revealed no $Te^o$, nor was any detected in the cytoplasmic or periplasmic fractions of either culture by this method. These results demonstrated conclusively that *R. sphaeroides* 2.4.1 could effect the intracellular reduction of $Te^{IV}$, which resulted in the deposition of metallic $Te^o$ in the cytoplasmic, but not intracytoplasmic, membrane.

Hydrogen Evolution From "Tellurite-Class" Oxyanion Reduction

Figure 1B:
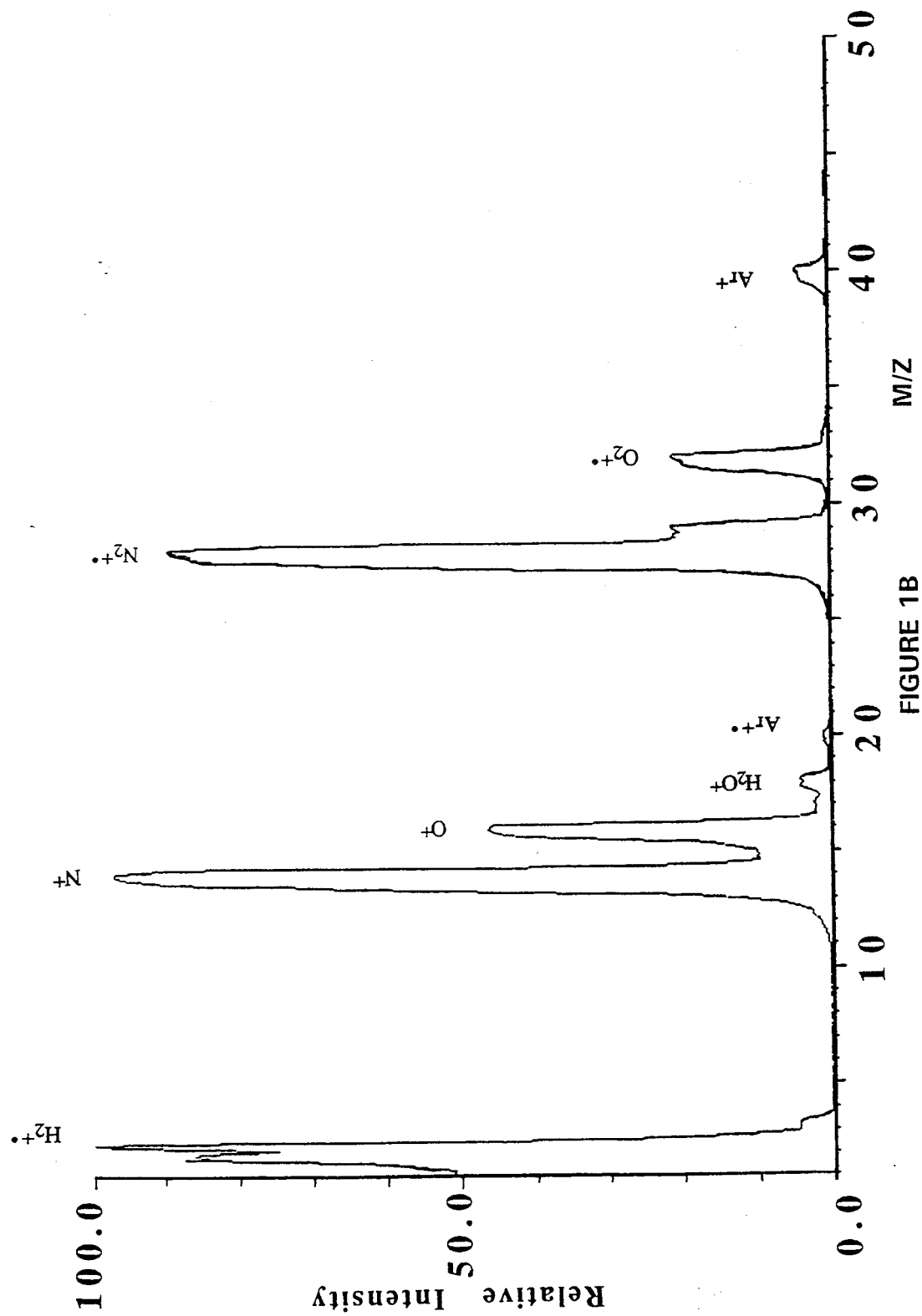
FIG. 1B is the mass spectrum of the headspace gas collected above photosynthetic (10 W/m² incident light intensity) cultures of *R. sphaeroides* grown in the presence of 25 µg/ml $K_2TeO_3$.

Although no gas was evolved from cells grown in the absence of $TeO_3^{2-}$, 208 ml of water was displaced from the gas collection vessel over the culture grown in the presence of $TeO_3^{2-}$. This corresponded to 8.37 mmole of gas (1 atm, 303° K.), the major component of which was subsequently identified as $H_2$ by mass spectroscopy, FIG. 1B. While ionization products of $H_2O$, $N_2$, and $CO_2$ were detected in both samples, no $H_2$ was detected in the headspace over the control culture, FIG. 1A. The trace amounts of Argon recorded in each spectra resulted from its use as a carrier in the analyses. Combined with earlier results, these data suggested approximately 11.5 mmoles of $H_2$ were evolved per mmole of $Te^o$ deposited.

EXAMPLE 6

The requirements for tellurite reduction in *R. sphaeroides* in vivo were determined by assaying tellurite resistance in a number of mutant strains.

Mechanism of $TeO_3^{2-}$ High Level Resistance in *R sphaeroides* 2.4.1

Several growth conditions were examined to determine requirements for tellurite reduction in vivo. Table 5 indicates the growth conditions tested.

As indicated in Table 5, neither the DMSO reductase, the B800–850 spectral complex, nor the B875 spectral complex was required to effect HLR to $TeO_3^{2-}$ under any growth condition examined. Deletion of the 42-kb endogenous plasmid of *R. sphaeroides* 2.4.1 did not diminish HLR to $TeO_3^{2-}$, although we did observe a 20% increase in $TeO_3^{2-}$ sensitivity in the carotenoid-deficient strain, 2.4.1-Ga.

A single mutation in either prkB or cfxB diminished HLR to $TeO_3^{2-}$ 10–20%, whereas strains deleted for either of their homologues, prkA or cfxA, were two-fold more sensitive to $TeO_3^{2-}$ under aerobic growth conditions, and at least three- to five-fold more sensitive under photosynthetic and anaerobic-dark/DMSO growth conditions.

Analyses of additional *R. sphaeroides* mutants determined the obligate requirement for an intact photosynthetic reaction center (RC) and a functional electron transport system for HLR to $TeO_3^{2-}$ when metabolic activities are carried out photosynthetically. These analyses also demonstrated that certain mutants, while unable to facilitate tellurite reduction, were resistant to intermediate concentrations of tellurite: viz a Bchl⁻ mutant (MM1006), a Puf⁻ mutant (PUFB1), and a strain deleted for cytochrome $c_2$ (CYCA1) were inhibited by 10 μg/ml K$_2$TeO$_3$ under anaerobic-dark/DMSO growth conditions, but were unaffected by the addition of tellurite under aerobic growth. Likewise, the photosynthetically-incompetent double--deletion strains, CFXA$^-$B$^-$ and PRKA$^-$B$^-$, while unable to effect TeO$_3^2$ reduction either inability of either to effect oxyanion reduction and metal sequestration in vivo.

Negligible reductase activity was observed in the periplasmic and cytoplasmic fractions of all strains, and in separate analyses, a TeO$_3^{2-}$-dependent oxidation of NADH or NADPH was not detected in subcellular

TABLE 5

Analysis of intrinsic HLR to tellurite in R. sphaeroides mutants.

| Strain | Relevant genotype/ phenotype | Photo-synthetic competence | MIC K$_2$TeO$_3$ (μg/ml)$^a$ | | |
|---|---|---|---|---|---|
| | | | Aerobic | Photosynthetic$^b$ 10 W/m$^2$ | Anaerobic$^-$ dark$^c$ |
| 2.4.1 | Wild-type | + | 900 | 600 | 150 |
| 2.4.1ΔS | Δ(42-kb plasmid) | + | 850 | 600 | 150 |
| 2 4.1-Ga | Car$^-$ | + | 600 | 450 | 100 |
| MM1004 | DORase$^-$ | + | 800 | 550 | NG |
| PUC705BA | B800-850$^-$ | + | 850 | 500 | 150 |
| PRKB$^-$ | PrkB$^-$ | + | 800 | 500 | 150 |
| CFXB$^-$ | CfxB$^-$ | + | 750 | 650 | 150 |
| CFXA$^-$ | CfxA$^-$ | + | 400 | 100 | 50 |
| PRKA$^-$ | PrkA$^-$ | + | 350 | 100 | 60 |
| MM1006 | Bchl$^-$ | — | (400)$^d$ | NG$^e$ | <10 |
| CYCA1 | Cyt c$_2^-$ | — | (400) | NG | <10 |
| PUFB1 | Puf$^-$ | — | (400) | NG | <10 |
| CFXA$^-$B$^-$ | CfxA$^-$, CfxB$^-$ | — | (200) | NG | <10 |
| PRKA$^-$B$^-$ | PrkA$^-$, PrkB$^-$ | — | (150) | NG | <10 |
| PUHA1 | RC-H$^-$, B875$^-$ | — | <10 | NG | <10 |
| BC17 | Car$^-$, Cyt bc$_1^-$ | — | <10 | NG | <10 |

$^a$MIC were determined in SMM containing succinate at 30° C.
$^b$Incident light intensity.
$^c$Supplemented with 60 mM DMSO.
$^d$() indicates resistance to TeO$_3^{2-}$, but no deposition of Te$^0$.
$^e$NG, no growth.

aerobically or anaerobically in the dark (in the presence of DMSO), were resistant to tellurite at concentrations <200 μg/ml under aerobic conditions. In contrast, strains lacking either the RC-H polypeptide (PUHA1) or the cytochrome bc$_1$ complex (BC17) were sensitive to 10 μg/ml K$_2$TeO$_3$ under all growth conditions.

EXAMPLE 7

The experiments in this example were aimed at determining the intracellular localization of tellurite reductase activity.

Tellurite Reductase Activity in Cell Free Extracts

Subcellular fractions of aerobically grown cells were prepared from wild-type and three mutant strains unable to reduce tellurite. These cells were grown in the absence of TeO$_3^2$, and were harvested during the mid-exponential phase of growth. This analysis, results of which are shown in Table 6, identified an FADH$_2$-dependent TeO$_3^{2-}$ reductase activity present in the membrane fraction of wild-type R. sphaeroides 2.4.1. Cells cultured in the presence of TeO$_3^{2-}$ also expressed similar TeO$_3^{2-}$-dependent FADH$_2$ oxidation activity in vitro. A specific activity of 300 nmole FADH$_2$/min per mg protein was detected in the membrane fraction of wild-type cells.

An FADH$_2$-dependent TeO$_3^{2-}$ reductase activity was also observed in the photosynthetically-incompetent strain PRKA$^-$B$^-$, despite this strain's inability to reduce TeO$_3^{2-}$ in vivo, see Table 5. This suggested that in addition to an FADH$_2$-dependent reductase, at least one other component was required to facilitate complete reduction to Te$^o$ in vivo.

Neither BC17 nor PUHA1, two mutants which were previously shown to be tellurite sensitive under both aerobic and anaerobic-dark/DMSO growth conditions, expressed significant levels of a TeO$_3^{2-}$-dependent FADH$_2$ oxidase activity in vitro. This may explain the fractions from any of these strains. This would not preclude, however, the participation of a NADH- or NADPH-dependent oxidation step in the reduction of an intermediate in the reduction of Te$^{IV}$ to Te$^o$.

EXAMPLE 8

This example illustrates the construction of a mutant R. sphaeroides from wild type strain 2.4.1.

R. sphaeroides 2.4.1ΔS

A mutant R. sphaeroides was prepared from wild type strain 2.4.1. R. sphaeroides 2.4.1Δs is a derivative of R. sphaeroides 2.4.1 which has been "cured" of one of its five endogenous plasmids, the 42-kb plasmid designated e (Fornari et al., 1984) or "S" factor (Suwanto and Kaplan, 1989 A; Suwanto and Kaplan, 1989 B; Suwanto and Kaplan, 1991).

The plasmid was readily cured by the introduction of either of the incompatibility determinants, Inca or IncB derived from native "S" factor on a selectable antibiotic resistance containing, unstable plasmid derivative. Once "S" was cured the introduced plasmid was readily lost following removal of the antibiotic selection. Two important features of 2.4.1Δs are that

TABLE 6

TeO$_3^{2-}$-dependent FADH$_2$ oxidation in R. sphaeroides 2.4.1.

| Strain$^a$ | Subcellular Fraction | FADH$_2$ oxidation$^b$ (nmole min$^{-1}$ mg$^{-1}$) |
|---|---|---|
| 2.4.1 | Periplasm | 1 |
| | Membrane | 300 |
| | Cytoplasm | 60 |
| BC17 | Periplasm | 2 |
| | Membrane | 51 |
| | Cytoplasm | 20 |
| PRKA$^-$B$^-$ | Periplasm | 3 |
| | Membrane | 200 |
| | Cytoplasm | 20 |

TABLE 6-continued

TeO$_3^{2-}$-dependent FADH$_2$ oxidation in *R. sphaeroides* 2.4.1.

| Strain[a] | Subcellular Fraction | FADH$_2$ oxidation[b] (nmole min$^{-1}$ mg$^{-1}$) |
|---|---|---|
| PUHA1 | Periplasm | 3 |
| | Membrane | 28 |
| | Cytoplasm | 37 |

[a]Cells were grown aerobically in SMM containing 0.4% succinate.
[b]100 µg/ml K$_2$TeO$_3$ was used in all assays.

the phenotype associated with oxyanion or metal oxide metabolism is not associated with the "S" factor and this strain may be used in conjugal genetic studies involving oriT mediated chromosome transfer.

REFERENCES

Chiong, M., Gonzalez, E., Barra, R. and Vasquez, C., *J. Bacteriol.* 170, 3269–3273 (1988).

Chiong, M., E. Gonzalez, R. Barra, and C. Vasquez, *J. Bacteriol.* 170:3269–3273 (1988).

Cohen-Bazire, G., W. R. Sistrom, and R. Y. Stanier, *J. Cell Comp. Physiol.* 49:25–68 (1956).

Davis, J., T. J. Donohue, and S. Kaplan, *J. Bacteriol.*, 170:320–329 (1988).

Donohue, T. J., B. D. Cain, and S. Kaplan, *J. Bacteriol,* 152:595–606 (1982).

Donohue, T. J., A. G. McEwan and S. Kaplan, *J Bacteriol.,* 168:962–972 (1986).

Donohue, T. J., A. G. McEwan, S. Van Doren, A. R. Crofts, and S. Kaplan, *Biochemistry,* 27:1918–1925 (1988).

Drews, G., and R. Biesbrecht, *Arch. Mikrobiol.,* 53:255–262 (1966).

Firsow, N. N., and G. Drews, *Arch. Microbiol.,* 115:299–306 (1977).

Fornari, C. S., Watkins, M., and Kaplan, S., *Plasmid* 11, 39–47 (1984).

Fraley, R. T., D. R. Leuking, and S. Kaplan *J. Biol. Chem.* 254:1980–1986 (1979).

Francis, A. J. and Gillow, J. B., U.S. Pat. No. 5,047,152, Sep. 10, 1991.

Gerrard, T. L., J. N. Telford, and H. H. Williams, *J. Bacteriol.,* 19:1057–1060 (1974).

Hallenbeck, P. L., R. Lerchen, P. Hessler, and S. Kaplan, *J. Bacteriol.* 172:1749–1761 (1990).

Hallenbeck, P. L., R. Lerchen, P. Hessler, and S. Kaplan, *J. Bacteriol.* 172:1736–1748 (1990).

Jeffery, G. H., J. Bassett, J. Mendham, and R. C. Denney, *Vogel's textbook of quantitative chemical analysis,* (1989).

Jobling, M. G., and D. A. Ritchie, *Gene,* 66:245–258 (1988).

Jobling, M. G., and D. A. Ritchie, *Mol. Gen. Genet.* 208:288–293 (1987).

Khalafalla, S., U.S. Pat. No. 4,910,010, Mar. 20, 1990.

Kiffney, P., and A. Knight, *Arch. Environ. Contam. Toxicol.,* 19:488–494 (1990).

Lee, J. K., P. J. Kiley, and S. Kaplan, *J. Bacteriol.,* 171:3391–3405 (1989).

Lowry, O. H., N. J. Rosebrough, A. L. Farr, and R. J. Randall, *J. Biol. Chem.,* 193:265–275 (1951).

Maniatis, T., E. F. Fritsch, and J. Sambrook, *Mollecular cloning: a laboratory manual.* (1982).

Markwell, M. A. S. M. Haas, L. L. Bieber, and N. E. Tolbert, *Anal. Biochem.,* 87:206 (1978).

Meinhardt, S. W., P. J. Kiley, S. Kaplan, A.R. Crofts, and S. Harayama, *Arch. Biochem. Biophys.,* 236:130–139 (1985).

Messing. J., *Recombinant DNA Tech. Bull.,* 2:43–48 (1979).

Moore, M. D., and S. Kaplan, *J. Bacteriol.,* 171:4385–4394 (1989).

Moore, M. D., and S. Kaplan, *Abstr. Annu. Meet. Am. Soc. Microbiol.* (1991).

Scala, J. and Williams, H., *Arch. Biochem. Biophys.* 99, 363–368 (1962).

Scala, J., and H. Williams, *Arch. Biochem. Biophys.,* 99:363–368 (1962).

Scala, J. and Williams, H., *Arch. Biochem. Biophys.* 101, 319–324 (1963).

Scala, J., and H. Williams, *Arch. Biochem. Biophys.,* 101:319–324 (1963).

Schroeder, H. A., Buckman, J. and Balassa, J. J., *J. Chronic Dis.* 20, 147–161 (1967).

Shepherd, W. D., and S. Kaplan. Unpublished observations.

Simon, R., U. Priefer, and A. Puhler, *Bio/Technology,* 1:37–45 (1983).

Sistrom, W. R., *J. Bacteriol.,* 131:526–532 (1977).

Sockett, R. E., T. J. Donohue, A. R. Varga, and S. Kaplan, *J. Bacteriol.,* 171:436–446 (1988).

Springer, S. E., and R. E. Huber *Arch. Biochem. Biophys.,* 156:595–603 (1973).

Stackebrandt, E., R. G. E. Murray, and H. G. Truper *Int. J. Syst. Bacteriol.* 38:321–325 (1988).

Steinberg, N. A., and R. S. Oremland, *Appl. Environ. Microbiol.* 56:3550–3557 (1990).

Summers, A. O. and Silver, S. *Ann. Rev. Microbiol.* 32 637–672 (1978).

Summers, A. O., and G. A. Jacoby, *J. Bacteriol.,* 129:276–281.

Summers, A. O., and S. Silver, *Ann. Rev. Microbiol.,* 32:637–672 (1978).

Summers, A. O. and Silver, S., *Ann. Rev. Microbiol.* 32, 637–672 (1978).

Suwanto, A. and Kaplan, S., *J. Bacteriol.* 171, 5840–5849 (1989 A).

Suwanto, A. and Kaplan, S., *J. Bacteriol.* 171, 5850–5859 (1989 B).

Sylvester, M. A., J. P. Deason, H. R. Feltz, and R. A. Engberg, In Proceedings on planning now for irrigation drainage studies, *Am. Soc. Civil Eng.,* New York p. 665–677 (1988).

Sylvester, M. A., Deason, J. P., Feltz, H. R. and Engberg, R. A., in Proceedings on planning now for irrigation drainage studies, *Am. Soc. Civil Eng.,* New York, 1988, pp 665–677.

Tai, T-N., M. D. Moore, and S. Kaplan, *Gene,* 70:139–151 (1988).

Taylor, D. E., E. G. Walter, R. Sherburne, and D. P. Bazett-Jones, *J. Ultrastruc. Mol. Struc. Res.,* 99:18–26 (1988).

Terai, T., T. Kamahora, and Y. Yamamura, *J. Bacteriol.,* 75:535–539 (1958).

Uffen, R. L., *Proc. Natl. Acad. Sci. USA,* 73:3298–3302 (1976).

Van Neil, B. B., *Bacteriol. Rev.,* 8:1–118 (1944).

Walter, E. G., C. M. Thomas, J. P. Ibbotson, and D. E. Taylor, *J. Bacteriol.,* 173:1111–1119 (1991).

Walter, E. G., J. H. Weiner, and D. E. Taylor, *Abstr. Annu. Meet. Am. Soc. Microbiol.,* p.321 (1991).

Walter, E. G. Thomas, C. M., Ibbotson, J. P. and Taylor, D. F., *J. Bacteriol.* 173, 1111–1119 (1991).

Walter, E. G. and Taylor, D. E., *J. Bacteriol.* 171, 2160–2165 (1989).

Walter, E.G., and D.E. Taylor, J. Bacteriol., 171:2160–2165 (1989).
Weaver, P. F., J. D. Wall, and H. Gest, *Arch. Microbiol.*, 105:207–216 (1975).
Weiss, R. L., *J. Bacteriol.*, 128:668–670 (1976).
Woese, C. R., W. G. Weisburg, C. M. Hahn, B. J. Paster, L. B. Zablen, B. J. Lewis, T. J. Macke, W. Ludwig, and E. Stackebrandt, *Syst. Appl. Microbiol.* 6:25–33 (1985).
Woese, C. R., W. G. Weisburg, B. J. Paster, C. M. Hahn, R. S. Tanner, N. R. Krieg, H-P, Koops, H. Harms, and E. Stackebrandt, *Syst. Appl. Microbiol.* 5:327–336 (1984).
Woese, C. R., E. Stackebrandt, W. G. Weisburg, B. J. Paster, M. T. Madigan, V. J. Fowler, C. M. Hahn, P. Blanz, R. Gupta, K. H. Nealson, and G. E. Fox *Syst. Appl. Microbiol.* 5:315–326 (1984).
Yen, H-C., and B. Marrs, *Arch. Biochem. Biophys.* 181:411–418 (1977).
Yun, C-H., R. Beici, A. R. Crofts, S. Kaplan, and R. B. Gennis, *Eur. J. Biochem.* 194:399–411 (1990).

What is claimed is:

1. A method for the reduction of a metal oxide or oxyanion, comprising contacting the metal oxide or oxyanion with a culture of photosynthetic Proteobacterium selected from a group consisting of Rhodobacter and Rhodopseudomonas in an aqueous medium under conditions facilitating reduction of the metal oxide or oxyanion by said Proteobacterium.

2. The method of claim 1 wherein the Rhodobacter is *R. sphaeroides* or *R. capsulatus*.

3. The method of claim 1 wherein the Rhodobacter is *Rhodobacter sphaeroides* 2.4.1 (ATCC 55398), 2.4.1ΔS (ATCC 49848) or 2.4.7 (ATCC 17028).

4. The method of claim 1 wherein the Rhodobacter is *R. capsulatus* B10 (ATCC 33303).

5. The method of claim 1 wherein the metal oxide or oxyanion is reduced to free metal.

6. The method of claim 1 wherein the metal oxide or oxyanion is a metal oxide or oxyanion of selenium, tellurium or rhodium.

7. The method of claim 6 wherein the metal oxide or oxyanion of selenium, tellurium or rhodium is tellurate, tellurite, selenate, selenite or rhodium sesquioxide.

8. The method of claim 1 wherein conditions facilitating reduction of the metal oxide or oxyanion comprise an aerobic environment.

9. The method of claim 1 wherein conditions facilitating reduction of the metal oxide or oxyanion comprise an anaerobic environment.

10. The method of claim 1 wherein conditions facilitating reduction of the metal oxide or oxyanion comprise minimal media having a carbon source in a low oxidation state.

11. The method of claim 10 wherein the carbon source is butyrate, succinate or malate.

12. The method of claim 1 wherein conditions facilitating reduction of the metal oxide or oxyanion comprise photoheterotrophic conditions.

13. The method of claim 12 wherein photoheterotrophic conditions include an incident light intensity of between about 5 and 25 W/m$^2$.

14. A method of reducing a metal or nonmetal oxide or oxyanion in aqueous medium, comprising growing Rhodobacter under suitable aerobic or anaerobic conditions minimal media having a carbon source in a low oxidation state and contacting a sample containing the metal or nonmetal oxide or oxyanion with the Rhodobacter to allow reduction of said oxide or oxyanion by said Rhodobacter.

15. The method of claim 14 wherein the carbon source is butyrate, succinate or malate.

16. The method of claim 14 wherein the minimal media contains about 0.2 to about 0.8% by weight of the carbon source.

17. The method of claim 14 wherein the metal or nonmetal is selected from a group consisting of silicon, molybdenum, arsenic, tungsten, tin, sulfur, antimony and vanadium.

18. A method of reducing an oxide or oxyanion of a metal comprising the steps:
   growing *R. sphaeroides* in an aerobic or anaerobic environment in minimal media:
   contacting the *R. sphaeroides* with a sample containing a metal oxide or oxyanion under conditions suitable for reduction of the metal oxide or oxyanion by *R. sphaeroides*: and
   isolating a *R. sphaeroides* cell or *R. sphaeroides* cell fraction which contains free metal resulting from reduction of said metal oxide or oxyanion.

19. The method of claim 18 wherein the *R. sphaeroides* is 2.4.1 (ATCC 55398) or 2.4.1ΔS (ATCC 49848).

20. The method of claim 18 wherein the cell fraction containing the free metal is the cell cytoplasmic membrane fraction.

21. The method of claim 18 wherein the metal is selected from a group consisting of gold, platinum, uranium, silver, palladium and titanium.

22. The method of claim 18 wherein the metal is selected from a group consisting of tellurium, selenium, and rhodium.

23. The method of claim 18 further comprising growing *R. sphaeroides* under photoheterotrophic conditions.

24. The method of claim 20 wherein the isolating is by sucrose density gradient centrifugation of the cytoplasmic membrane fraction.

25. The method of claim 18 wherein the sample is obtained from surficial sediments, groundwater, salina, estuarial salterns, farm drainage, streams, rivers, ponds, marine waters or littoral lakes.

26. A method of isolating free metal from a solution containing an oxide or oxyanion of the metal, comprising:
   reducing the metal oxide or oxyanion under conditions suitable for reduction of the metal oxide or oxyanion by the cytoplasmic membrane fraction of *R. sphaeroides* 2.4.1 (ATCC 55398) to produce free metal;
   accumulating the free metal in said membrane fraction; and
   separating the free metal from the membrane fraction in which the free metal has accumulated to obtain substantiality pure metal.

* * * * *

UNITED STATES PATENT AND TRADEMARK OFFICE
CERTIFICATE OF CORRECTION

PATENT NO. : 5,352,608  
DATED : October 4, 1994  
INVENTOR(S) : Kaplan et al

Page 1 of 3

It is certified that error appears in the above-indentified patent and that said Letters Patent is hereby corrected as shown below:

Title page, item [56], column 2, line 21, delete "Phylozenatic" and insert --Phylogenetic-- therefor.

Title page, item [56], column 2, line 22, delete "Systemic" and insert --Systematic-- therefor.

Page 2, column 2, line 8, delete "Compound,"" and insert --Compounds," -- therefor.

Page 2, column 2, line 22, delete "PHH1508a,"" and insert --pHH1508a," -- therefor.

In column 1, line 31, delete "oxyanlons" and insert --oxyanions-- therefor.

In column 3, line 40, delete "/peptone" and insert --peptone,-- therefor.

In column 3, line 50, delete "tryprone" and insert --tryptone-- therefor.

In column 4, line 14, delete "proteobacteria" and insert --Proteobacteria-- therefor.

In column 4, line 28, delete "facilitatina" and insert --facilitating-- therefor.

In column 4, line 43, delete "molybendum," and insert --molybdenum,-- therefor.

In column 4, line 46, delete "$Rh_2O.5H_2O$," and insert --$Rh_2O \cdot 5H_2O$,-- therefor.

In column 4, line 52, delete "$\Delta s$" and insert --$\Delta S$-- therefor.

In column 5, line 2, delete "proteobacteria" and insert --Proteobacteria-- therefor.

UNITED STATES PATENT AND TRADEMARK OFFICE
CERTIFICATE OF CORRECTION

PATENT NO. : 5,352,608  Page 2 of 3
DATED : October 4, 1994
INVENTOR(S) : Kaplan et al

It is certified that error appears in the above-indentified patent and that said Letters Patent is hereby corrected as shown below:

In column 6, line 2, delete "of 250/µg/ml".

In column 6, line 5, delete "25" and insert --250-- therefor.

In column 6, line 9, delete "proteobacteria" and insert --Proteobacteria-- therefor.

In column 9, line 5, delete "1" and insert --1.-- therefor.

In column 9, line 50, delete "$Rh_2O_3.5H_2O$," and insert --$Rh_2O_3 \cdot 5H_2O$,-- therefor.

In column 11, line 14, delete "2.4.1As," and insert --2.4.1∆S,-- therefor.

In column 12, line 6, delete "2.4.1∆s," and insert --2.4.1∆S,-- therefor.

Col. 12, lines 22-23, delete "proteobacteria" and insert Proteobacteria-- therefor.

In column 12, line 23, delete "metaloxide" and insert --metal oxide-- therefor.

In column 12, line 67, delete "$Rh_2O_3.5H_2O$" and insert --$Rh_2O_3 \cdot 5H_2O$-- therefor.

In column 13, line 15, delete "$SiO^4{}_2{}_-$" and insert --$SiO_4{}^{2-}$-- therefor.

In column 16, line 51, delete "Inca" and insert --IncA-- therefor.

In column 16, line 56, delete "2.4.1∆s" and insert --2.4.1∆S-- therefor.

UNITED STATES PATENT AND TRADEMARK OFFICE
CERTIFICATE OF CORRECTION

PATENT NO. : 5,352,608
DATED : October 4, 1994
INVENTOR(S) : Kaplan et al

It is certified that error appears in the above-indentified patent and that said Letters Patent is hereby corrected as shown below:

In column 17, line 31, delete "Biesbrecht," and insert --Giesbrecht,-- therefor.

In claim 1, column 19, line 26, delete "Rhodobacter" and insert --*Rhodobacter*-- therefor.

In claim 1, column 19, line 27, delete "Rhodopseudomonas" and insert --*Rhodopseudomonas*-- therefor.

Col. 20, lines 3-4, delete "conditions" and insert --conditions in-- therefor.

Signed and Sealed this

Twentieth Day of December, 1994

Attest:

BRUCE LEHMAN

Attesting Officer    Commissioner of Patents and Trademarks